United States Patent [19]

Kukolja et al.

[11] Patent Number: 4,683,227
[45] Date of Patent: Jul. 28, 1987

[54] ANTIBIOTIC DERIVATIVES OF 7β-[2-(THIAZOL-4-YL)ACETAMIDE]-3-CHLORO-3-CEPHEM-4-CARBOXYLIC ACIDS AND COMPOSITIONS AND METHOD OF USE THEREOF

[75] Inventors: Stjepan Kukolja, Carmel; Walter E. Wright, Indianapolis, both of Ind.

[73] Assignee: Eli Lilly and Company, Indianapolis, Ind.

[21] Appl. No.: 753,291

[22] Filed: Jul. 9, 1985

[51] Int. Cl.⁴ .................. A61K 31/545; C07D 501/20
[52] U.S. Cl. ..................................... 514/202; 540/222
[58] Field of Search .......................... 544/22; 514/202

[56] References Cited

U.S. PATENT DOCUMENTS

| | | | |
|---|---|---|---|
| 3,268,523 | 8/1966 | Raap, I | 544/22 |
| 3,322,749 | 5/1967 | Crast, I | 544/22 |
| 3,322,751 | 5/1967 | Crast, II | 544/22 |
| 3,468,874 | 9/1969 | Raap, II | 544/22 |
| 3,627,760 | 12/1971 | Binningen | 544/22 |
| 3,962,227 | 6/1976 | Chauvette | 544/22 |
| 4,267,176 | 5/1981 | Kamiya et al. | 544/22 |
| 4,370,326 | 1/1983 | Takaya | 544/22 |
| 4,411,897 | 10/1983 | Scartazzini et al. | 540/222 |
| 4,465,668 | 8/1984 | Nishikido, I | 544/22 |

FOREIGN PATENT DOCUMENTS 0068403 1/1983 European Pat. Off. .

OTHER PUBLICATIONS

Dunn J. Antimicrobial Chemotherapy (1982) 10, Supple. C pp. 1–10.
J. A. Webber and W. J. Wheeler, "Chemistry and Biology of Beta-Lactam Antibiotics vol. 1, Penicillins and Cephalosporins", R. B. Morin et al., Ed., Academic Press, N.Y, 1982, Chap. 4, pp. 391–397.
J. A. Webber et al., in "Structure Activity Relationships Among the Semisynthetic Antibiotics", Academic Press, Inc., N.Y., 1977, pp. 170–182.

*Primary Examiner*—Robert J. Warden
*Assistant Examiner*—Robert Benson
*Attorney, Agent, or Firm*—William B. Scanlon; Leroy Whitaker

[57] ABSTRACT

7β-Heterocyclicacetylamino-(and 7β-heterocyclicthioacetamido)-3-chloro-3-cephem-4-carboxylic acids and pharmaceutically acceptable salts thereof, e.g., 7β-[2-(2-aminothiazol-4-yl)acetamido]-3-chloro-3-cephem-4-carboxylic acid and salts thereof, exhibit surprising peroral bioavailability and are useful in a method for treating infections in man and animals and in formulations for oral administration.

9 Claims, No Drawings

ANTIBIOTIC DERIVATIVES OF 7β-[2-(THIAZOL-4-YL)ACETAMIDE]-3-CHLORO-3-CEPHEM-4-CARBOXYLIC ACIDS AND COMPOSITIONS AND METHOD OF USE THEREOF

BACKGROUND OF THE INVENTION

This invention relates to a method for the treatment of infectious diseases in man and animals. In particular, it relates to a method for the treatment of bacterial infections in man and animals which comprises administering by the oral route certain heteroarylacylamido-3-chloro-substituted cephalosporins. Also provided are pharmaceutical formulations for oral therapy and 3-halo-substituted cephalosporins useful in the peroral treatment method.

Since the discovery of cephalosporin C by E. P. Abraham, a wide variety of structurally distinct cephalosporin antibiotics have been prepared and evaluated. A number of these broad spectrum cephalosporins have achieved clinical importance among which are cephalothin, cephaloridine, cefazolin, cephamandole, cefoxitin, cephapirin, ceftazidime, cefotaxime, cefuroxime, cephalexin, and cefaclor.

The cephalosporin antibiotics as a class, with the exceptions noted below, are generally recognized as being poorly absorbed from the gastrointestinal tract and, accordingly, are administered parenterally. Despite the wide variety of structurally distinct cephalosporins that have been prepared and evaluated, little is known regarding the structural features required to imbue a cephalosporin with the property of ready absorption from the gastrointestinal tract.

The exceptions to the above are represented by the antibiotics cephalexin, cefaclor, and cephradine. These antibiotics exhibit high absorption from the gastrointestinal tract and thus are effective when taken orally. Structurally, these antibiotics have either the phenylglycyl group or the structurally similar 1,4-cyclohexadienylglycyl group as the 7-position side chain. Likewise, other cephalosporins having such an arylglycyl group in the 7-position are shown to exhibit absorption by the oral route. Consequently, it has become generally recognized that a structural feature required for high oral absorption is an arylglycyl 7-position side chain or a close analog thereof.

Chauvette describes in U.S. Pat. No. 4,064,343, 3-chloro-7β-acylamido-3-cephem-4-carboxylic acid compounds as antibiotics. In column 25 of the patent, Chauvette teaches the parenteral administration, i.e., subcutaneously or intramuscularly, of these non-arylglycyl substituted compounds. In contrast, in U.S. Pat. No. 3,925,372, Chauvette describes cefaclor and related compounds and their effectiveness when administered orally. Structurally, cefaclor contains the D-phenylglycyl group, an arylglycyl moiety, as the side chain in the 7-position of the cephem nucleus.

The present invention comprises the discovery that certain 3-chloro-substituted cephalosporins having a non-arylglycyl side chain demonstrate surprising peroral bioavailability.

DETAILED DESCRIPTION

The invention comprises in one of its aspects a method for the treatment of bacterial infections in man and animals which comprises administering to the infected host, by the oral route, a 3-chloro-substituted cephalosporin represented by the formula 1

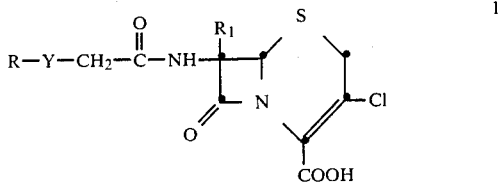

wherein R is a 5-membered heterocyclic nitrogen-containing ring represented by the formulae

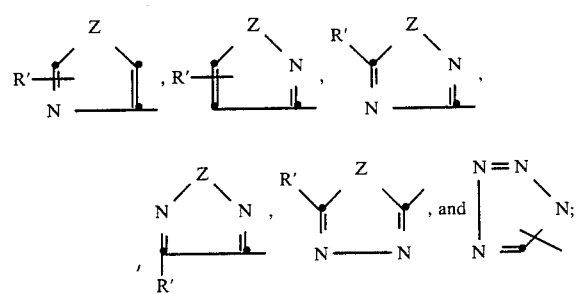

Y is S or a bond;
where in the above formula, Z is O, S, or N and R' is hydrogen, hydroxy, halo, cyano, amino, $C_1$–$C_4$ alkanoylamino, $C_1$–$C_4$ alkylamino, di-($C_1$–$C_4$ alkyl)amino, $C_1$–$C_4$ alkylsulfonylamino, $C_1$–$C_4$ alkanoyloxy, $C_1$–$C_4$ alkoxy, $C_1$–$C_4$ alkylsulfonyloxy, $C_1$–$C_4$ alkyl, phenyl, or trihalomethyl;

$R_1$ is hydrogen, methoxy, or formamido; and the pharmaceutically acceptable non-toxic salts thereof.

The 5-membered heterocyclic ring

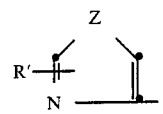

in the formula 1 represents an oxazole, thiazole, or imidazole ring;

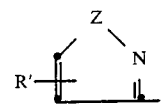

an isoxazole, isothiazole, or pyrazole ring;

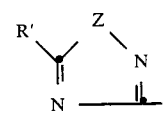

a 1,2,4-oxadiazole, 1,2,4-thiadiazole, or 1,2,4-triazole ring;

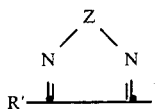

a 1,2,5-oxadiazole, 1,2,5-thiadiazole, or 1,2,3-triazole ring;

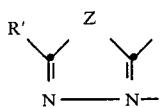

a 1,3,4-oxadiazole, 1,3,4-thiadiazole, or 1,3,4-triazole ring; or a 1H-tetrazole ring; wherein such 5-membered rings are optionally substituted.

Optional substituents represented by R' in the formula 1 are, for example, hydroxy; halo, preferably fluoro or chloro; amino; $C_1$-$C_4$ alkanoylamino such as acetylamino, propionylamino, or pivaloyl; $C_1$-$C_4$ alkylamino such as methylamino, ethylamino, or n-butylamino; di($C_1$-$C_4$ alkyl)amino such as dimethylamino, diethylamino, methylethylamino, or di-n-butylamino; $C_1$-$C_4$ alkylsulfonylamino such as methylsulfonylamino, ethylsulfonylamino, or n-butylsulfonylamino; $C_1$-$C_4$ alkanoyloxy such as acetoxy, propionyloxy, butyryloxy, or pivaloyloxy; $C_1$-$C_4$ alkoxy such as methoxy, propoxy, iso-propoxy, or n-butoxy; $C_1$-$C_4$ alkylsulfonyloxy such as methylsulfonyloxy, ethylsulfonyloxy, or n-butylsulfonyloxy; $C_1$-$C_4$ alkyl such as methyl, ethyl, n-propyl, iso-propyl, n-butyl, or sec-butyl; phenyl, and trihalomethyl such as trichloromethyl and trifluoromethyl.

Examples of heteroaryl groups R include thiazole, 2-methylthiazol-4-yl, 2-chlorothiazol-4-yl, 2-hydroxythiazol-4-yl, 2-aminothiazole-4-yl, 2-methyloxazol-4-yl, 2-phenyloxazol-4-yl, 4-phenylisothiazol-3-yl, 4-ethylisothiazol-3-yl, 4-aminooxazol-3-yl, 4-methylisoxazol-3-yl, 4-trifluoromethylisoxazol-3-yl, 4-dimethylamino-1,2,5-oxadiazol-3-yl, 4-acetylamino-1,2,5-oxadiazol-3-yl, 4-chloro-1,2,5-oxadiazol-3-yl, 4-methoxy-1,2,5-oxadiazol-3-yl, 4-methyl-1,2,5-thiadiazol-3-yl, 4-acetylamino-1,2,5-thiadiazol-3-yl, 4-chloro-1,2,5-thiadiazol-3-yl, 5-methyl-1,2,4-oxadiazol-3-yl, 5-amino-1,2,4-oxadiazol-3-yl, 5-amino-1,2,4-thiadiazol-3-yl, 5-chloro-1,2,4-thiadiazol-3-yl, 5-phenyl-1,2,4-thiadiazol-3-yl, 5-acetylamino-1,2,4-thiadiazol-3-yl, 5-methylsulfonylamino-1,2,4-thiadiazol-3-yl, 5-ethoxy-1,2,4-thiadiazol-3-yl, 5-methyl-1,3,4-oxadiazol-2-yl, 5-amino-1,3,4-oxadiazol-2-yl, 5-amino-1,3,4-thiadiazol-2-yl, 5-chloro-1,3,4-thiadiazol-2-yl, 5-hydroxy-1,3,4-thiadiazol-2-yl, 5-acetylamino-1,3,4-thiadiazol-2-yl, 5-methoxy-1,3,4-thiadiazol-2-yl, 5-methyl-1,3,4-triazol-2-yl, 5-phenyl-1,3,4-triazol-2-yl, 1,3,4-triazol-2-yl, 1,2,3-triazol-4-yl, 5-ethyl-1,2,3-triazol-4-yl, 5-methoxy-1,2,4-triazol-3-yl, 5-dimethylamino-1,2,4-triazol-3-yl, 5-acetoxy-1,2,4-triazol-3-yl, 4-trifluoromethylimidazol-3-yl, 5-phenylimidazol-3-yl, 5-aminoimidazol-3-yl, 2-aminopyrazol-4-yl, 5-aminopyrazol-4-yl, 2-methoxypyrazol-4-yl, pyrazole-4-yl, 1H tetrazol-1-yl, and like unsubstituted and optionally substituted heterocyclic rings.

The 3-chloro-substituted cephalosporins represented by the formula 1 are prepared by known methods. Preferably, they are prepared by the N-acylation of 7-amino-3-chloro-3-cephem-4-carboxylic acid or a carboxy-protected ester derivative thereof. Chauvette describes this 3-chloro nucleus compound in U.S. Pat. No. 4,064,343 and the N-acylation thereof by a number of methods. One such method by which the compounds of formula 1 may be prepared comprises N-acylation of the 3-chloro nucleus with a heterocyclic acetic acid in the form of an active derivative of the carboxy group. Active carboxy derivatives are, for example, the acid halides such as the acid chloride or bromide; the acid azides; the active esters such as those formed with N-hydroxysuccinimide, hydroxybenztriazole, and the like; active esters such as pentachlorophenyl ester; the mixed anhydride esters formed with the acetic acid as the sodium salt, and a chloroformate ester such as ethyl chloroformate and isobutyl chloroformate; and dehydrative coupling carried out with the acetic acid and the 7-amino-3-chloro nucleus and a diimide, e.g., dicyclohexylcarbodiimide.

The following reaction scheme illustrates the N-acylation of the 7-amino-3-chloro nucleus compound with a heterocyclic acid chloride.

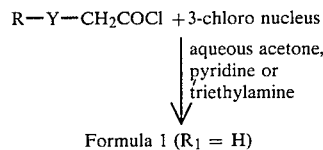

The compounds represented by the formula 1 wherein Y is S also can be prepared by reacting the heterocyclic thiol R-SH with a 7β-haloacetylamino-3-chloro-3-cephem-4-carboxylic acid ester. The reaction is carried out under basic conditions to provide the salt form of the thiol eg the sodium salt. For example, p-nitrobenzyl 7β-bromoacetylamino-3-chloro-3-cephem-4-carboxylate is reacted with 2-methylthiazol-4-thiol in basic medium to provide p-nitrobenzyl 7β-[2-(2-methylthiazol-4-yl)thioacetylamino]-3-chloro-3-cephem-4-carboxylate. Deesterification of the p-nitrobenzyl group provides the antibiotic free acid.

The compounds represented by the formula 1 wherein $R_1$ is methoxy are obtained with the compound of the formula 1 wherein $R_1$ is H by the 7-methoxylation method described by Yanagisawa et al., *Tetrahedron Letters* (1975) 2705.

Preferred compounds for use in the method of this invention are represented by the formula 1 wherein $R_1$ is hydrogen. A further preferred group of compounds are represented when $R_1$ is hydrogen, Y is a bond and R is a thiazole and oxadiazole ring.

An especially preferred group of 3-chloro-substituted cephalosporins is represented by the formula 1 wherein R is an optionally substituted thiazole group, Y is a bond and $R_1$ is hydrogen. An especially preferred compound is 7β-[2-(2-aminothiazol-4-yl)acetamido]-3-chloro-3-cephem-4-carboxylic acid. Also preferred are the corresponding 2-methyl- and 2-chloro-substituted thiazol-4-yl-3-chloro compounds.

Pharmaceutically acceptable salts of the compounds of formula 1 are the non-toxic salts formed with suitable bases in conventional salt-forming methods. Suitable bases include inorganic bases such as the alkali metal and alkaline earth metal hydroxides, carbonates and bicarbonates, e.g., sodium hydroxide, potassium hydroxide, calcium hydroxide, sodium carbonate, and sodium bicarbonate. Organic amines are suitable bases for forming amine salts. Amines such as benzylamine, dibenzylamine, diethylamine, di-(n-butyl)amine, 2-hydroxyethylamine, di-(2-hydroxyethyl)amine, di-(3-hydroxypropyl)amine, methylamine, dicyclohexylamine, procaine, and abietylamine may be used. Likewise, salts formed with the amino acids such as lysine and arginine may be used.

The peroral bioavailability of the 3-chloro cephalosporins represented by the formula 1 is demonstrated in mice in tests carried out as follows:

Cox Male Standard Mice, Lai:COX (Standard) BR were housed overnight in a wire-bottom cage with free access to water and liquid diet. The result was a gastrointestinal tract free of solids, yet without the nutritional shock and coprophagy that often accompanies overnight starvation of rodents. After dosing, the mice were housed individually in ventilated wide-mouth jars containing a layer of buffer beneath an elevated wire screen floor. At intervals after dosing, mice were removed from the jars and heparinized blood, stomach, and small intestine were removed from the animals. The urinary bladder was removed and combined with the urine collected in the buffer in the bottom of the jars. Urine, washings from the stomach and small intestine, and plasma prepared from blood samples were assayed for antibiotic activity. The test procedure used is a modification of the test procedure described by W. E. Wright, et al., *J. Antibiotics*, 32:1155 (1979).

Dose solutions were prepared in saline at 2 mg/ml for subcutaneous or oral administration. In all cases the compounds were administered to the mice at 20 mg/kg on an equal weight basis.

The biological activity of the samples was determined by a conventional agar well procedure using *Bacillus subtilis* ATCC 6633 as the test organism.

Peroral bioavailability (BA) of the test compounds in mice can be determined either by comparison of the area under the plasma curves (AUC) after oral or subcutaneous dosage, or by comparison of the urinary excretion of the dose after oral and subcutaneous dosage. Calculations of BA by either method are made with the following formulae:

$$\frac{AUC \text{ after oral dose}}{AUC \text{ after s.c. dose}} \times 100 = \% BA (AUC)$$

$$\frac{\text{Percent of dose in urine after p.o.}}{\text{Percent of dose in urine after s.c.}} \times 100 = \% BA (URINE)$$

The percent bioavailability obtained in mice for three preferred compounds is tabulated below wherein R and $R_1$ have reference to formula 1.

| Test Compound | | Oral Bioavailability | |
|---|---|---|---|
| R (Y = —) | $R_1$ | % BA (URINE) | % BA (AUC) |
| 2-aminothiazol-4-yl | H | 64 | 62 |
| 2-methylthiazol-4-yl | H | 66 | 57 |
| 2-chlorothiazol-4-yl | H | 56 | 66 |

The peroral bioavailability also is shown in dogs. In tests carried out in female mongrel dogs and the bioavailability calculated with the above-described formulae, the preferred compound 7β-[2-(2-aminothiazol-4-yl)acetamido]-3-chloro-3-cephem-4-carboxylic acid showed a bioavailability of 28%. Penicillin V, a well known oral antibiotic, in the same test showed oral bioavailability of 11% calculated by determining the area under the curves obtained by measuring serum antibacterial levels with time following both intravenous and oral administration. The bioavailability for penicillin V was 21% when calculated by determining the percent of dose recovered in the urine with time following both intravenous and oral administration.

The method of this invention is useful in treating infections caused by a variety of microorganisms pathogenic to man and animals. In Table 1 below are listed the minimum inhibitory concentrations (mic) exhibited by compounds of the invention against gram-positive and gram-negative bacteria. The concentrations were obtained by the standard agar dilution method.

TABLE 1

Antibacterial Activity of Heterocyclicacetamido-3-chloro Cephalosporins

| | | Minimum Inhibitory Concentration (μg/ml)[1] 3-chloro compound[2] | | | | | | |
|---|---|---|---|---|---|---|---|---|
| Test Organism | Strain | 1 | 2 | 3 | 4 | 5 | 6 | 7 |
| *Staphylococcus aureus* | X1.1 | 4 | 1 | 1 | 1 | 0.25 | 2 | 2 |
| *Staphylococcus aureus* | V41 | 128 | 32 | 64 | 128 | 32 | 32 | 128 |
| *Staphylococcus aureus* | X400 | 128+ | 128+ | 128+ | 128+ | 64 | 128+ | 128+ |
| *Staphylococcus aureus* | S13E | 64 | 32 | 64 | 128 | 16 | 32 | 128 |
| *Staphylococcus epidermidis* | Epi1 | 16 | 4 | 8 | 8 | 4 | 16 | 8 |
| *Staphylococcus epidermidis* | 222 | 4 | 1 | 2 | 2 | 0.5 | 4 | 4 |
| *Streptococcus pyogenes* | C203 | 1 | 0.06 | 0.25 | 0.25 | 0.06 | 0.5 | 0.25 |
| *Streptococcus pneumoniae* | PARK I | 2 | 0.5 | 0.5 | 1 | 0.125 | 0.5 | 0.5 |
| Streptococcus sp. group D | X66 | 128+ | 128+ | 128 | 128+ | 64 | 64 | 128 |
| Streptococcus sp. group D | 2041 | 128 | 32 | 64 | 128 | 16 | 64 | 64 |
| *Haemophilus influenzae* | C.L. | 4 | 0.5 | 2 | 2 | 4 | 16 | 2 |
| *Haemophilus influenzae* | 76 | 4 | 0.5 | 2 | 1 | 0.5 | 8 | 2 |
| *Escherichia coli* | N10 | 32 | 4 | 32 | 32 | 128+ | 32 | 64 |
| *Escherichia coli* | EC14 | 8 | 1 | 16 | 16 | 128+ | 16 | 32 |
| *Escherichia coli* | TEM | 16 | 2 | 16 | 16 | 128+ | 32 | 64 |
| *Klebsiella pneumoniae* | X26 | 4 | 0.25 | 4 | 2 | 8 | 32 | 32 |
| *Klebsiella pneumoniae* | KAE | 128+ | 16 | 128 | 128+ | 128+ | 128+ | 128+ |
| *Klebsiella pneumoniae* | X68 | 8 | .5 | 8 | 8 | 128+ | 32 | 64 |

[1] +indicates higher than.
[2] Test compounds, Nos. 1-8 are represented by the formula 1 as follows:

| Compound No. | R |
|---|---|
| 1 | 5-amino-1,2,4-thiadiazol-3-yl |
| 2 | 2-aminothiazol-4-yl |
| 3 | 2-chlorothiazol-4-yl |

-continued

| Compound No. | R |
| --- | --- |
| 4 | 2-methylthiazol-4-yl |
| 5 | 2-phenylthiazol-4-yl |
| 6 | 1H—tetrazole-1-yl |
| 7 | 3-cyano-1H—1,2,4-triazol-1-yl |

According to the method of this invention, a 3-chloro-substituted cephalosporin represented by the formula 1 is administered by the oral route to man and animals in the treatment of bacterial infections. The 3-chloro compound as the free acid or, preferably, a pharmaceutically acceptable, non-toxic salt thereof is administered in a dose of between about 50 mg and 2,000 mg. The regimen of treatment may vary depending upon such factors as the severity of the infection, the particular infecting organism or organisms, the age and general health of the host, and the sensitivity of the particular host to the antibiotic. The antibiotic may be administered in a single daily dose or, preferably, in multiple doses throughout the day, e.g., bid, tid., or qid. Treatment may be indicated for up to 10 days or 2 weeks.

The method may be employed in the prophylactic treatment of a susceptible or jeopardized host, for instance, in preventing the reoccurrence of rheumatic fever, or in the preoperative setting.

The 3-chloro antibiotics may be administered in formulations suitable for oral administration. Suitable formulations include capsules, tablets, lozenges, liquid suspensions, and the like.

This invention also provides pharmaceutical formulations useful for oral administration which comprise a compound represented by the formula 1 and at least one orally acceptable carrier. A preferred formulation of this invention comprises a compound of the formula 1 in gelatin capsules. Tablet formulations are prepared in a conventional manner and may contain fillers, binders, coating agents, stabilizing agents, antioxidants, lubricants for tableting, flavoring agents, disintegrators, and the like. For example, suitable oral carriers include starch such as corn starch, sugars such as glucose, fructose, or mannose, talc, alginic acid, magnesium stearate, stearic acid, ascorbic acid, and like carriers.

For liquid suspensions the 3-chloro compound may be formulated with an orally acceptable liquid such as water, ethyl alcohol, an edible vegetable oil such as soybean oil, and contain a suspending agent, flavoring agent, a sugar such as dextrose, a thickening agent, preservative such as sodium benzoate, and like additives.

Preferred formulations of this invention are capsules and tablets in unit dosage form. Unit dosages may be made up by filling capsules with the desired dosage. Capsules containing 100 mg, 250 mg, and 500 mg of the 3-chloro compound are preferred. Unit dosages in tablet form can contain 100 mg, 200 mg, or 300 mg of 3-chloro compound per tablet.

As was mentioned hereinabove, certain 3-chloro compounds of this invention are preferred. These novel preferred compounds are represented by the formula 1 wherein R is an oxazole or thiazole ring represented by the formula

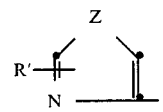

wherein Z is O or S, R' has the same meanings as defined for formula 1, Y is a bond —, and $R_1$ is hydrogen. Especially preferred compounds are represented when R' is hydrogen, $C_1$–$C_4$ alkyl, halo, or amino. The compounds represented when Z is S are further preferred. Examples of the above-defined preferred compounds are:

7β-[2-(2-aminothiazol-4-yl)acetamido]-3-chloro-3-cephem-4-carboxylic acid,

7β-[2-(2-chlorothiazol-4-yl)acetamido]-3-chloro-3-cephem-4-carboxylic acid,

7β-[2-(2-methylthiazol-4-yl)acetamido]-3-chloro-3-cephem-4-carboxylic acid,

7β-[2-(thiazol-4-yl)acetamido]-3-chloro-3-cephem-4-carboxylic acid, and

7β-[2-(2-ethyloxazol-4-yl)acetamido]-3-chloro-3-cephem-4-carboxylic acid, and the pharmaceutically acceptable non-toxic salts thereof. Preferred salts are the sodium and potassium salts.

Preferred formulations of this invention comprise a preferred 3-chloro compound in unit dosage form in capsules or tablets. One such preferred formulation comprises 250 mg of 7β-[2-(2-aminothiazol-4-yl)acetamido]-3-chloro-3-cephem-4-carboxylic acid in capsule form. Another preferred formulation comprises 500 mg of 7β-[2-(2-chlorothiazol-4-yl)acetamido]-3-chloro-3-cephem-4-carboxylic acid sodium salt in capsule form. A further preferred formulation comprises 300 mg of 7β-[2-(2-methylthiazol-4-yl)acetamido]-3-chloro-3-cephem-4-carboxylic acid sodium salt in tablet form.

It will be recognized that the compounds represented by the formula 1 wherein R' is an amino group substituent can form acid addition salts with suitable acids such as hydrochloric acid, hydrobromic acid, sulfuric acid, or phosphoric acid. Such acid addition salts are pharmaceutically acceptable for oral administration and may be used in the formulations and method of this invention.

The following Examples are provided to further illustrate the practice of this invention.

EXAMPLE 1

7β-[2-(2-Methylthiazol-4-yl)acetamido]-3-chloro-3-cephem-4-carboxylic acid

A. Preparation of 2-methylthiazol-4-yl acetic acid.

Ethyl 2-methylthiazol-4-yl acetate, 1.94 g (10 mmole) was stirred with 25 ml of a 10% aqueous solution of potassium hydroxide for 10 minutes. The solution was acidified to pH 2.5 with 50% aqueous hydrochloric acid and the solution extracted three times with ethyl acetate. The extracts were combined, dried over magnesium sulfate and slowly evaporated until crystallization occurred. The crystalline acid was filtered and washed with diethyl ether to provide a first crop of acid of 612 mg melting at about 124° to about 125° C. and a second crop of 31.2 mg.

B. Acylation of 3-Chloro Nucleus.

The 2-methylthiazol-4-yl acetic acid, 628 mg, prepared as described above, was suspended in 20 ml of benzene and the solution treated with 1.2 ml of oxalyl chloride and one drop of dimethylformamide. The reaction mixture was stirred until solution was obtained (ca. 30 minutes) and was then evaporated to remove benzene and excess oxalyl chloride. In a separate flask a solution of 1.1 g of 7β-amino-3-chloro-3-cephem-4-carboxylic acid was formed in a mixture of acetone and water (20 ml/20 ml, v/v) with 1 g of sodium bicarbonate. The solution of the 3-chloro nucleus sodium salt was cooled in an ice bath and a solution of the acid chloride in 20 ml of acetone was added to the cold nucleus solution by dropwise addition. After the addition was complete, the reaction mixture was stirred for about 2 hours while the reaction mixture warmed to room temperature. After the acylation was complete as indicated by thin layer chromatography (4:1, ethyl acetate:acetic acid, v:v), the reaction mixture was evaporated and the aqueous phase was extracted with ethyl acetate. The aqueous phase was then layered with fresh ethyl acetate and the pH of the aqueous phase adjusted to 2.5 with 1N hydrochloric acid. The insoluble material which precipitated was filtered and discarded. The aqueous layer was separated and reextracted with fresh ethyl acetate. The extracts were combined, dried over magnesium sulfate, and evaporated. The residue containing the acylation product was chromatographed over a column packed with silica gel using chloroform to 5% methanol in chloroform to separate the small amount of unreacted side chain from the title compound.

EXAMPLE 2

7β-[2-(2-Chlorothiazol-4-yl)acetamido]-3-chloro-3-cephem-4-carboxylic acid

A. Preparation of 2-Chlorothiazol-4-yl Acetic Acid Chloride.

Ethyl 2-chlorothiazol-4-yl acetate, 1.1 g (5.3 mmoles) was stirred in a solution of 10 ml of ethyl alcohol containing 5 ml of 2.22N sodium hydroxide until saponification was complete. The ethyl alcohol was evaporated from the reaction mixture, ethyl acetate was added to the aqueous residue, and the pH was adjusted to 2.5 with 1N hydrochloric acid. The ethyl acetate layer was separated, dried over magnesium sulfate, and evaporated to dryness. Benzene, 25 ml, oxalyl chloride, 1.5 ml, and one drop of DMF were added to the residue, and the mixture was stirred until all solids were in solution. The reaction mixture was then evaporated to remove excess oxalyl chloride and benzene to provide the acid chloride.

B. Acylation of 3-Chloro Nucleus.

The acid chloride prepared above was then used to acylate 1.4 g of the 3-chloro nucleus in aqueous acetone by following the acylation procedure described in Example 1. The acylation reaction mixture was stirred overnight and following recovery of the crude acylation product as described in Example 1, the product was dissolved in chloroform, stirred with charcoal, and filtered through a filter aid. The chloroform was evaporated and the product was recrystallized from ethyl acetate.

EXAMPLE 3

7β-[2-(2-Phenylthiazol-4-yl)acetamido]-3-chloro-3-cephem-4-carboxylic acid

A. Preparation of 2-Phenylthiazol-4-yl Acetic Acid.

A solution of 2.3 g of ethyl chloroacetoacetate and 2.5 g of thiobenzamide in 25 ml of absolute ethyl alcohol was heated at the reflux temperature for about 12 hours. One hundred milliliters of 1N hydrochloric acid was added to the reaction mixture to form the hydrochloride salt. Since the product failed to form the hydrochloride salt, the product was extracted with ethyl acetate. The extract was chromatographed on silica gel and diluted with toluene to provide 2.6 g of ethyl 2-phenylthiazol-4-yl acetate.

The ester, 2.6 g, was stirred in a mixture of 35 ml of 10% potassium hydroxide and 25 ml of ethyl alcohol for about 12 hours to saponify the ethyl ester. The reaction mixture was extracted three times with diethyl ether and the aqueous portion acidified to pH 2 with about 10 ml of 50% hydrochloric acid. The acidified solution was extracted three times with diethyl ether, the extracts combined, dried over magnesium sulfate, and evaporated to dryness. There were obtained 2.3 g of 2-phenylthiazol-4-yl acetic acid as an orange oil.

B. N-Acylation of 3-Chloro Nucleus.

The 2-phenylthiazol-4-yl acetic acid, 1.16 g, was converted to the acid chloride with 1.6 ml of oxalyl chloride in 25 ml of benzene containing one drop of DMF. The acid chloride was then used to acylate 1.5 g of the 3-chloro nucleus in aqueous acetone in the presence of 1.4 g of sodium bicarbonate to provide the title compound.

EXAMPLE 4

7β-[2-(2-Aminothiazol-4-yl)acetamido]-3-chloro-3-cephem-4-carboxylic acid

A. Preparation of 2-Triphenylmethylaminothiazol-4-yl Acetyl Chloride.

Into 600 ml of methylene chloride cooled to a temperature between about −20° C. to about 30° C. was passed chlorine gas while a solution of 49.5 ml of triphenylphosphite in 50 ml of methylene chloride was added dropwise. The rate of addition of the phosphite was controlled to maintain the temperature below about −10° C. and to maintain an excess of chlorine, as indicated by the yellow-green color of the solution. After the addition was complete, the solution is purged with nitrogen and the excess chlorine is destroyed by the addition of excess amylene to the solution.

To the solution of the triphenylphosphite chlorine complex is added portionwise 62.5 g of 2-tritylaminothiazol-4-yl acetic acid. The formation of the acid chloride is accompanied by an exotherm and, accordingly, the reaction mixture is recooled and maintained at a temperature of about −10° C. The reaction mixture is stirred for about 45 minutes to complete formation of the acid chloride.

B. N-Acylation of 3-Chloro Nucleus.

To 450 ml of dimethylformamide is added 36.9 g of 7-amino-3-chloro-3-cephem-4-carboxylic acid and 35.2 g of bistrimethylsilylurea and the mixture is stirred at room temperature until solution is obtained. The solution is cooled to a temperature of about −10° C. and 28 ml of pyridine is added to the solution just prior to addition of the acid chloride prepared as described above. The solution of the acid chloride is chilled prior to addition so that upon addition the temperature of the acylation mixture does not exceed 10° C. Once addition of the acid chloride is complete, the reaction mixture is cooled to about −5° C. and stirred for about 30 minutes.

The reaction mixture was diluted with 200 ml of methylene chloride and 2000 of water were added. The mixture was shaken, the layers separated, and the aqueous layer was extracted with 300 ml of methylene chloride. The extract was combined with the organic layer and 200 ml of ethyl acetate is added to the methylene chloride layer to induce crystallization. The mixture is stirred at room temperature and then for 1 hour at about 0° C. to 5° C. The crystalline acylation product was filtered, washed with ethyl acetate, and dried in vacuo to provide 7β-[2-(2-triphenylmethylaminothiazol-4-yl)acetamido]-3-chloro-3-cephem-4-carboxylic acid in a yield of about 80%.

The acylation product, 84.7 g, is added to 325 ml of 98% formic acid at a temperature of about 10° C. to about 15° C. and the mixture is stirred until a solution is obtained. The solution is then warmed to about room temperature and stirring is continued for about 2 hours. After the reaction is complete, the insoluble triphenylcarbanol is filtered and washed with formic acid. The wash and filtrate are combined and stirred with charcoal for about 30 minutes. The solution is filtered to remove the charcoal and is then poured slowly into acetone with stirring at room temperature. Stirring is continued for about 1 hour at room temperature, the solution cooled to about 0° C. to 5° C. and stirring is continued for about an hour. The crystalline title compound which forms is filtered, drenched with cold acetone, and dried. The title compound is generally obtained as an off-white crystalline solid in about a 90% yield.

EXAMPLE 5

In following the procedures described in the foregoing Examples, the following 3-chloro compounds are prepared:
(a) 7β-[2-(4-aminoisothiazol-3-yl)acetamido]-3-chloro-3-cephem-4-carboxylic acid.
(b) 7β-[2-(5-chloro-1,3,4-oxadiazol-2-yl)acetamido]-3-chloro-3-cephem-4-carboxylic acid.
(c) 7β-[2-(5-methyl-1,2,4-thiadiazol-3-yl)acetamido]-3-chloro-3-cephem-4-carboxylic acid.
(d) 7β-[2-(2-aminoimidazol-3-yl)acetamido]-3-chloro-3-cephem-4-carboxylic acid.
(e) 7β-[2-(5-fluoro-1,3,4-triazol-2-yl)acetamido]-3-chloro-3-cephem-4-carboxylic acid.
(f) 7β-[2-(2-methylthiazol-4-yl)thioacetamido]-3-chloro-3-cephem-4-carboxylic acid.

EXAMPLE 6

Sodium 7β-[2-(2-Methylthiazol-4-yl)acetamido]-3-chloro-3-cephem-4-carboxylate, 300 mg, is formulated into tablet form with starch and magnesium stearate.

EXAMPLE 7

7β-[2-(2-Aminothiazol-4-yl)acetamido]-3-chloro-3-cephem-4-carboxylic acid as a dry crystalline powder is filled in 250 mg portions into gelatin capsules to provide 250 mg unit dosages.

EXAMPLE 8

7β-[2-(2-Chlorothiazol-4-yl)acetamido]-3-chloro-3-cephem-4-carboxylic acid is filled in 500 mg portions into gelatin capsules to provide 500 mg unit dosages.

EXAMPLE 9

7β-[2-(2-Aminooxazol-4-yl)acetamido]-3-chloro-3-cephem-4-carboxylic acid as a dry powder is filled in 250 mg portions into gelatin capsules to form 250 mg unit dosages.

We claim:
1. The compound of the formula

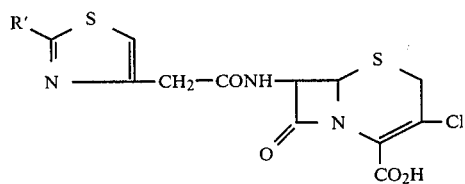

wherein R' is chloro or methyl, and the pharmaceutically acceptable non-toxic salts thereof.

2. The compound of claim 1 which is 7β-[2-(2-chlorothiazol-4-yl)acetamido]-3-chloro-3-cephem-4-carboxylic acid.

3. The compound of claim 1 which is 7β-[2-(2-methylthiazol-4-yl)acetamido]-3-chloro-3-cephem-4-carboxylic acid.

4. An antibiotic formulation suitable for oral administration which comprises an antibacterially effective amount of a compound of claim 1 or a pharmaceutically acceptable non-toxic salt thereof and a pharmaceutically acceptable carrier.

5. The formulation of claim 4 comprising the antibiotic 7β-[2-(2-chlorothiazol-4-yl)acetamido]-3-chloro-3-cephem-4-carboxylic acid or the pharmaceutically acceptable salts thereof.

6. The formulation of claim 4 comprising the antibiotic 7β-[2-(2-methylthiazol-4-yl)acetamido]-3-chloro-3-cephem-4-carboxylic acid or the pharmaceutically acceptable salts thereof.

7. The method for treating infections in man and animals which comprises administering to said host, by the oral route, an antibacterially effective amount of a compound of the formula

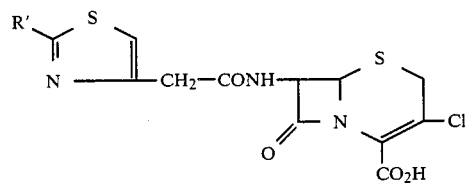

wherein R' is chloro or methyl, or a pharmaceutically acceptable non-toxic salt thereof.

8. The method of claim 7 wherein 7β-[2-(2-chlorothiazol-4-yl)acetamido]-3-chloro-3-cephem-4-carboxylic acid or a pharmaceutically acceptable salt thereof is administered.

9. The method of claim 7 wherein 7β-[2-(2-methylthiazol-4-yl)acetamido]-3-chloro-3-cephem-4-carboxylic acid or a pharmaceutically acceptable salt thereof is administered.

* * * * *